United States Patent
Kleemiss

(12) 
(10) Patent No.: US 6,248,917 B1
(45) Date of Patent: Jun. 19, 2001

(54) PROCESS FOR THE PREPARATION OF 2-HYDROXYBENZONITRILE

(75) Inventor: Wolfgang Kleemiss, Haltern (DE)

(73) Assignee: Huels Aktiengesellschaft, Marl (DE)

( * ) Notice: Subject to any disclaimer, the term of this patent is extended or adjusted under 35 U.S.C. 154(b) by 0 days.

(21) Appl. No.: 08/663,661

(22) Filed: Jun. 14, 1996

(30) Foreign Application Priority Data

Jun. 21, 1995 (DE) .............................................. 195 22 430

(51) Int. Cl.$^7$ .................................................. C07C 253/20
(52) U.S. Cl. ............................................. 558/312; 558/311
(58) Field of Search ..................................... 558/311, 312

(56) References Cited

FOREIGN PATENT DOCUMENTS 2 020 866    11/1971   (DE) .
710973       6/1954    (GB) .

OTHER PUBLICATIONS

Patent Abstracts of Japan, vol. 13, No. 49 (C–565), Feb. 3, 1989, JP–A–63 243064, Oct. 7, 1988.

Masaru Ogata et al, "Reaction Of N,N'–Carbonyldiimidazole and N,N'–Thionyldiimidazole With Amides: An Imidazole Transfer Reaction", Heterocycles, vol. 12, No. 10, 1979, pp. 1284–1289.

Chemical Abstracts, published by the American Chemical Society, vol. 108, 1988, Abstract No. 74939h.

Khuong Mai et al, "Facile Conversion Of Carboxamides To Nitriles", Tetrahedron Letters, vol. 27, No. 20, 1986, pp. 2203–2206.

*Primary Examiner*—Floyd D. Higel
(74) *Attorney, Agent, or Firm*—Oblon, Spivak, McClelland, Maier & Neustadt, P.C.

(57) ABSTRACT

2-Hydroxybenzonitrile is prepared by passing 2-hydroxybenzamide in the gas phase over a heterogeneous catalyst thereby effecting dehydration of the 2-hydroxybenzamide to produce 2-hydroxybenzonitrile.

10 Claims, 1 Drawing Sheet

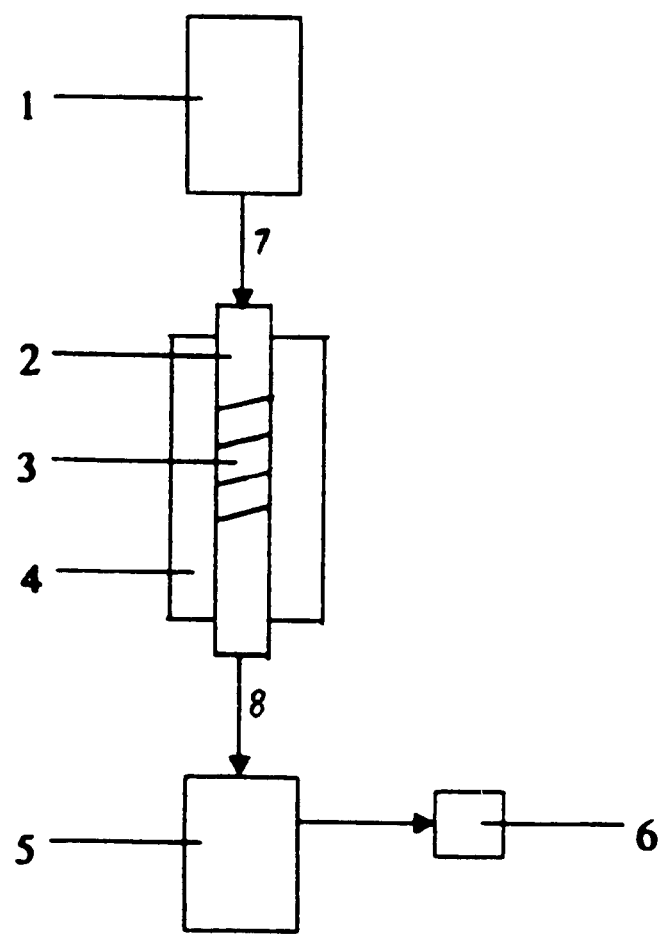

PROCESS FOR THE PREPARATION OF 2-HYDROXYBENZONITRILE

BACKGROUND OF THE INVENTION

Field of the Invention

The present invention relates to a process for the preparation of 2-hydroxybenzonitrile by dehydration of 2-hydroxybenzamide in the gas phase.

DESCRIPTION OF THE BACKGROUND

2-Hydroxybenzonitrile is an important intermediate for the preparation of biologically active substances.

The preparation of 2-hydroxybenzonitrile from 2-hydroxybenzamide is known in principle. However, only expensive reagents are described as dehydrating agents, which, moreover, must further be used in stoichiometric or superstoichiometric amounts.

Japanese patent application JP 12 301/66 discloses the reaction of, for example, 2-hydroxybenzamide with phosphorus chloride nitrides at 100 to 600° C.

DE-A 25 33 245 teaches the preparation of 2-hydroxybenzonitrile by reaction of the amide with phosgene in a nonpolar solvent. The nitrile is obtained in this reaction in a yield of >90%. Apart from the fact that phosgene must be used here in superstoichiometric amounts, the use of phosgene in industrial processes is associated with considerable difficulties because of its extreme toxicity.

The use of thiophosphoric diamide (Bull. Soc. Chim. Belg. 86, 4 (1977)), thionyldiimidazole (Heterocycles 12, 1285 (1979)) and trichloromethyl chloroformate (Tetrahedron Lett. 2203 (1986)) as dehydrating agents is also known for the preparation of 2-hydroxybenzonitrile from 2-hydroxybenzamide.

All of the methods described supra are only suitable for preparation of dehydrated products on the laboratory scale, since the reagents required are expensive and, furthermore, must be used in stoichiometric or superstoichiometric amounts.

Another reaction which is known is the catalytic reaction of methyl 2-hydroxybenzoate with ammonia to give 2-hydroxybenzonitrile (Izv. Akad. Nauk. Kaz. SSR, Ser. Khim. 1987 (2), 62). The catalyst used in this case is boron phosphate. A problem in this process is the formation of methylamine from ammonia and methanol which originates from the methyl ester. In addition, 2-hydroxybenzonitrile has the tendency to convert irreversibly at temperatures of >100° C. in the liquid phase into a high-melting triazine. That is, the 2-hydroxybenzonitrile which is formed reacts further in the hot reactor predominantly to give triazine. The product yield is therefore poor. Furthermore, this procedure is not suitable as an industrial process, since the reactor clogs within a short time. A need therefore continues to exist for an improved, industrially acceptable method of dehydrating amide compounds to the corresponding nitrites.

SUMMARY OF THE INVENTION

Accordingly, one object of the present invention is to provide a simple and economical process of dehydrating 2-hydroxybenzamide to 2-hydroxybenzonitrile in good yields.

Briefly, this object and other objects of the invention as hereinafter will become more readily apparent can be attained in a method of preparing 2-hydroxybenzonitrile by passing 2-hydroxybenzamide in the gas phase over a solid catalyst, thereby effecting dehydration of the 2-hydroxybenzamide to the corresponding nitrile product.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

The FIGURE is a diagram of the apparatus employed in the dehydration reaction of the invention.

DETAILED DESCRIPTION OF THE PREFERRED EMBODIMENTS

Surprisingly, it has been found that the dehydration of 2-hydroxybenzamide to 2-hydroxybenzonitrile can be carried out by heterogeneous catalysis in the gas phase with particularly good success. A particularly suitable catalyst is a silica gel impregnated with phosphoric acid. In a suitable manner, the catalyst impregnated with phosphoric acid is dried before use. A particularly suitable support is, for example, AF 125 (Kali-Chemie). However, other silica gel quality grades of comparable specification can also be used.

The dehydration reaction of the invention is preferably carried out at a temperature ranging from 200 to 400° C. The reaction is carried out in a suitable manner under reduced pressure. A surprising discovery is that the secondary reaction of 2-hydroxybenzonitrile to give a high-melting triazine compound does not take place if the reaction is preferably carried out at a pressure ranging from 5 to 100 mbar, particularly preferably from 20 to 40 mbar. Preferably, the reaction is carried out at an LHSV (liquid hourly space velocity) between 0.05 and 1 $h^{-1}$, particularly preferably between 0.1 and 0.5 $h^{-1}$. The crude output from the dehydration reaction, in addition to reaction water, contains more than 90% by weight of 2-hydroxybenzonitrile. Pure 2-hydroxybenzonitrile is obtained in a suitable manner by distillation, with vacuum distillation being preferred.

The process of the present invention is characterized by the use of a heterogeneous catalyst to promote the dehydration of 2-hydroxybenzamide to 2-hydroxybenzonitrile in the gas phase. The catalyst, which is used in the process of the invention, can be any one of a variety of shapes including spheres, beads, chips, strands, tubes or even as a monolith, for example, in a honeycomb shape. However, the catalyst can also be employed in powder form. Generally, the catalyst employed is an oxide catalyst comprised of aluminum oxide, silicon oxide, titanium oxide, zirconium oxide, silicates and various combinations of the oxides. Such oxide materials are then normally treated with an inorganic acid such as phosphoric acid, and then subjected to a thermal post-treatment.

The reaction of the invention is expediently conducted in a tubular reactor. In a suitable manner, the dehydration reaction is conducted in such a way that the catalyst, a silica gel impregnated with phosphoric acid, preferably with aqueous 5 to 85% strength by weight phosphoric acid, is first heated to a temperature of 200 to 500° C., preferably 300 to 400° C., particularly preferably 380 to 390° C. The 2-hydroxybenzamide can be added to the catalyst in the molten state, in which case the LHSV should be between 0.05 to 1 $h^{-1}$, preferably between 0.1 and 0.5 $h^{-1}$.

The present dehydration reaction is conducted in a suitable manner under reduced pressure, preferably at a pressure ranging from 5 to 100 mbar, particularly preferably at a pressure ranging from 20 to 40 mbar. The crude product thus obtained, also termed the crude output, is generally purified by distillation, preferably under vacuum, in which case the distillation should proceed without high thermal stressing of the 2-hydroxybenzonitrile, since the product has a tendency to form a high-melting triazine.

The FIGURE of the present application is a diagram of the experimental apparatus employed to conduct the dehydration reaction of the invention. In the process 2-hydroxybenzamide starting material, in starting material reservoir 1, which can be heated, is passed through line 7 into tubular reactor 2 which contains catalyst 3. The tubular reactor 1 is provided within heating jacket 4. Dehydration of the 2-hydroxybenzamide starting material occurs as the starting material, in the gas phase, contacts the solid catalyst in the reactor. The product produced is discharged from the reactor through line 8 into product receiving vessel 5. A reduced pressure atmosphere is provided in the system by vacuum pump 6.

The process of the present invention provides the possibility of preparing 2-hydroxybenzonitrile in a simple and economical manner.

Having generally described this invention, a further understanding can be obtained by reference to certain specific examples which are provided herein for purposes of illustration only and are not intended to be limiting unless otherwise specified.

EXAMPLE 1

Preparation of the Dehydration Catalyst:

A 200 g amount of silica gel (AF 125 from Kali-Chemie, Hannover) is stirred with 500 g of 30% strength by weight phosphoric acid for 2 h at room temperature. The solids are removed by filtration and then dried at 110° C. for 30 h.

Carrying out the Dehydration Reaction

Referring to the apparatus shown in the FIGURE discussed above, an 80 g (0.58 mol) amount of 2-hydroxybenzamide is melted in the heatable starting material reservoir (inlet temperature: 150° C.). At a pressure of 30 mbar and a catalyst temperature of 380 to 390° C., the liquid amide is metered (approximately 15 ml/h) into the tubular reactor onto the catalyst (catalyst volume: 100 ml). The LHSV is 0.15 h$^{-1}$. A 76 g amount of crude output is obtained from the experimental system.

The crude output obtained was distilled in a conventional distillation apparatus in order to purify the product. The data obtained are shown in Table I.

TABLE I

| Fraction | BT [° C.] | TT [° C.] | P [mbar] | m (g) | m.p. [° C.] |
|---|---|---|---|---|---|
| 1 | 60 | — | 0.07 | 9.5 | — |
| 2 | 120–173 | 46–173 | 0.1 | 62.3 | 80–84 |
| RS | — | — | — | 2.4 | >140 |
|  |  |  |  | 74.2 |  |

BT = bottom temperature
CT = cold trap
TT = top temperature
P = pressure
RS = residue
m.p. = melting point
m = mass Fraction 2 comprises 97% by weight of 2-hydroxybenzonitrile. The yield of 2-hydroxybenzonitrile is thus 87%.

EXAMPLE 2

A 210 g (1.53 mol) amount of 2-hydroxybenzamide is melted in a heatable reservoir (inlet temperature: 150° C.). At a pressure of 20 mbar and a catalyst temperature of 380 to 400° C., the liquid amide is metered (approximately 20 ml/h) onto the catalyst (catalyst volume: 100 ml, catalyst preparation cf. Example 1). The LHSV is 0.2 h$^{-1}$. A 202 g amount of a crude output was obtained from the catalyst furnace.

Distillation of the crude output is conducted in a simple distillation apparatus and the data obtained are shown in Table II.

TABLE II

| Fraction | BT [° C.] | TT [° C.] | P [mbar] | m (g) | m.p. [° C.] |
|---|---|---|---|---|---|
| 1 | 60 | — | 0.08 | 10 | — |
| 2 | 120–175 | 50–172 | 0.1 | 163 | 80–85 |
| RS | — | — | — | 20 | — |
| CT | — | — | — | 5 | — |
|  |  |  |  | 198 |  |

Fraction 2 comprises 97% by weight of 2-hydroxybenzonitrile. The yield of 2-hydroxybenzonitrile is thus 87%.

EXAMPLE 3

A 150 g (1.09 mol) amount of 2-hydroxybenzamide is melted in a heatable reservoir (inlet temperature: 150° C.). At a pressure of 30 mbar and a catalyst temperature of 380 to 390° C., the liquid amide is metered (approximately 10 ml/h) onto the catalyst (catalyst volume: 100 ml, catalyst preparation cf. Example 1). The LHSV is 0.1 h$^{-1}$. A 145 g amount of crude output was obtained.

Distillation of the crude output is then conducted in a simple distillation apparatus and the results obtained are shown in Table III.

TABLE III

| Fraction | BT [° C.] | TT [° C.] | P [mbar] | m (g) | m.p. [° C.] |
|---|---|---|---|---|---|
| 1 | 65 | — | 0.1 | 6 | — |
| 2 | 125–175 | 50–170 | 0.1 | 114 | 79–83 |
| RS | — | — | — | 15 | — |
| CT | — | — | — | 5 | — |
|  |  |  |  | 140 |  |

Fraction 2 comprises 97% by weight of 2-hydroxybenzonitrile. The yield is thus 85%.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing 2-hydroxybenzonitrile by a dehydration reaction, comprising:
    passing 2-hydroxybenzamide in the gas phase at a pressure of 5 to 100 mbar over a solid heterogenous catalyst at an LHSV of 0.05 to 1 h$^{-1}$, thereby obtaining a crude dehydration product containing 2-hydroxybenzonitrile.

2. The process according to claim 1, wherein said solid heterogeneous catalyst is a silica gel impregnated with phosphoric acid.

3. The process according to claim 2, wherein the said phosphoric acid impregnated silica gel is dried before use.

4. The process according to claim 1, wherein the reaction is conducted at a temperature ranging from 200 to 400° C.

5. the process according to claim 1, wherein the reaction is conducted at a pressure ranging from 20 to 40 mbar.

6. The process according to claim 1, wherein the reaction is conducted at an LHSV of 0.1 to 0.5 $h^{-1}$.

7. The process according to claim 1, which further comprises distilling said crude output product to obtain purified 2-hydroxybenzonitrile.

8. The process according to claim 1, wherein the solid, heterogeneous catalyst is bead shaped, spherical, monolithic in structure or is in the shape of chips, strands or tubes.

9. The process according to claim 1, wherein the catalyst is comprised of an oxide selected from the group consisting of aluminum oxide, silicon oxide, titanium oxide, zirconium oxide, a silicate and a mixture of at least two of the oxides.

10. The process according to claim 9, wherein said oxide catalyst is treated with an inorganic acid.

* * * * *